US006284874B1

(12) United States Patent
Taniguchi et al.

(10) Patent No.: US 6,284,874 B1
(45) Date of Patent: Sep. 4, 2001

(54) PROCESS FOR SEPARATING $\alpha_1$-PROTEINASE INHIBITOR FROM COHN FRACTION $IV_1$ AND $IV_4$ PASTE

(75) Inventors: T. (Tom) Taniguchi, Arcadia; John M. Rolf, Los Angeles; Prabir Bhattacharya, Walnut; Yahiro (Roy) Uemura, Arcadia, all of CA (US)

(73) Assignee: Alpha Therapeutic Corporation, Los Angeles, CA (US)

( * ) Notice: Subject to any disclaimer, the term of this patent is extended or adjusted under 35 U.S.C. 154(b) by 0 days.

(21) Appl. No.: 08/261,406

(22) Filed: Jun. 17, 1994

(51) Int. Cl.$^7$ .................................................. C07K 14/81
(52) U.S. Cl. ..................... 530/420; 530/412; 530/415; 530/416; 530/421
(58) Field of Search .................. 530/380, 381, 530/392, 395, 414, 416, 418, 419, 421, 415, 420, 422, 427

(56) References Cited

U.S. PATENT DOCUMENTS

| | | | |
|---|---|---|---|
| 4,379,087 | 4/1983 | Coan et al. ........................... | 530/380 |
| 4,439,358 | 3/1984 | Coan et al. ........................... | 530/392 |
| 4,540,573 | * 9/1985 | Neurath et al. ...................... | 530/381 |
| 4,629,567 | * 12/1986 | Bollen et al. ........................ | 210/635 |
| 4,656,254 | 4/1987 | Shearer et al. ...................... | 530/393 |
| 4,684,723 | 8/1987 | Dove et al. .......................... | 530/351 |
| 4,734,279 | 3/1988 | Stephan et al. ..................... | 424/85.5 |
| 4,829,054 | 5/1989 | Emerson, Jr. et al. ............... | 514/21 |
| 5,093,316 | 3/1992 | Lezdey et al. ....................... | 514/8 |
| 5,276,141 | * 1/1994 | Kolbe et al. ......................... | 530/395 |

OTHER PUBLICATIONS

Bischoff et al. "Purification & Biochemical Characterization of Recombinant, $\alpha_1$Antitrypsin Variant Expressed in *Escherichia coli*" Biochemistry 30 3464–3472 1991.*

Ng et al. "Plasma Protein Recovery From Spent Tissue Culture Fluid" Biotech Lett. 13(4) 261–264 1991.*

Harris et al. "Protein Purification Methods" 154–170 1989.*

Burnouf et al. Biochemical & Biological Properties of an $\alpha_1$–Antitrypsin Concentrate Vox Sang. 52 291–297 1987.*

Miles Inc., "Alpha$_1$–Proteinase Inhibitor (Human)," Rev. Mar. 1992.

Robin W. Carrell, "Reactive–Centre Variants of $\alpha_1$–Antitrypsin. A New Range of Anti–inflammatory Agents," *Biotechnology and Genetic Engineering Reviews*, vol. 4, Gordon E. Russell, ed., pp. 291–309.

M.H. Coan et al., "Preparation and Properties of Alpha$_1$–Proteinase Inhibitor Concentrate from Human Plasma," *Vox Sanguinis*, vol. 48, 1985, pp. 333–342.

Tai–Tung Yip and T. William Hutchens, "Immobilized Metal Ion Affinity Chromatography," *Methods in Molecular Biology, vol. 11: Practical Protein Chromatography*, A. Kenney and S. Fowell, eds., 1992, pp. 17–31.

* cited by examiner

*Primary Examiner*—Robert A. Schwartzman
(74) *Attorney, Agent, or Firm*—Christie, Parker & Hale, LLP

(57) ABSTRACT

The present invention is directed to a process for purifying $\alpha_1$-proteinase inhibitor. The process comprises providing an impure protein fraction which comprises $\alpha_1$-proteinase inhibitor. The impure protein fraction is precipitated with a precipitant comprising PEG. The supernatant from the PEG precipitation, which comprises $\alpha_1$-proteinase inhibitor, is collected and applied to an anion-exchange medium. A fraction comprising $\alpha_1$-proteinase inhibitor is recovered from the anion-exchange medium and applied to a metal chelate medium. A fraction comprising $\alpha_1$-proteinase inhibitor is then recovered from the metal chelate medium. Alpha$_1$-proteinase inhibitor purified by the process has a specific activity greater than 0.6 units/mg.

1 Claim, No Drawings

PROCESS FOR SEPARATING $\alpha_1$-PROTEINASE INHIBITOR FROM COHN FRACTION $IV_1$ AND $IV_4$ PASTE

FIELD OF THE INVENTION

The present invention relates to the purification of a serine proteinase inhibitor, $\alpha_1$-proteinase inhibitor.

BACKGROUND OF THE INVENTION

Alpha$_1$-Proteinase Inhibitor ($\alpha_1$-PI), also known as $\alpha_1$-antitrypsin, is a serum glycoprotein with a molecular weight of 52,000. Alpha$_1$-PI is synthesized in the liver and is present in the serum at levels between 150 and 350 mg/dl (equivalent to 30–80 $\mu$M) when assayed with plasma standards.

Alpha$_1$-PI functions in the lungs to inhibit neutrophil elastase, a serine protease, which in large quantities can lead to the destruction of the alveolar walls. In the normal lung, $\alpha_1$-PI provides more than 90% of the anti-neutrophil elastase protection in the lower respiratory tract.

Alpha$_1$-PI deficiency is an autosomal, recessive hereditary disorder displayed by a large number of allelic variants and has been characterized into an allelic arrangement designated as the protease inhibitor (Pi) system. These alleles have been grouped on the basis of the $\alpha_1$-PI levels that occur in the serum of different individuals. Normal individuals have normal serum levels of $\alpha_1$-PI (normal individuals have been designated as having a PiMM phenotype). Deficient individuals have serum $\alpha_1$-PI levels of less than 35% of the average normal level (these individuals have been designated as having a PiZZ phenotype). Null individuals have undetectable $\alpha_1$-PI protein in their serum (these individuals have been designated as having a Pi(null) (null) phenotype).

Alpha$_1$-PI deficiency is characterized by low serum (less than 35% of average normal levels) and lung levels of $\alpha_1$-PI. These deficient individuals have a high risk of developing panacinar emphysema. This emphysema predominates in individuals who exhibit PiZZ, PiZ(null) and Pi(null) (null) phenotypes. Symptoms of the condition usually manifests in afflicted individuals in the third to fourth decades of life.

The emphysema associated with $\alpha_1$-PI deficiency develops as a result of insufficient $\alpha_1$-PI concentrations in the lower respiratory tract to inhibit neutrophil elastase, leading to destruction of the connective tissue framework of the lung parenchyma. Individuals with $\alpha_1$-PI deficiency have little protection against the neutrophil elastase released by the neutrophils in their lower respiratory tract. This imbalance of protease:protease inhibitor in $\alpha_1$-PI deficient individuals results in chronic damage to, and ultimately destruction of the lung parenchyma and alveolar walls.

Individuals with severe $\alpha_1$-PI deficiency typically exhibit endogenous serum $\alpha_1$-PI levels of less than 50 mg/dl, as determined by commercial standards. Individuals with these low serum $\alpha_1$-PI levels have greater than an 80% risk of developing emphysema over a lifetime. It is estimated that at least 40,000 patients in the United States, or 2% of all those with emphysema, have this disease resulting from a defect in the gene coding for $\alpha_1$-PI. A deficiency in $\alpha_1$-PI represents one of the most common lethal hereditary disorders of Caucasians in the United States and Europe.

Therapy for patients with $\alpha_1$-PI deficiency is directed towards replacement or augmentation of $\alpha_1$-PI levels in the serum. If serum levels of $\alpha_1$-PI are increased, this is expected to lead to higher concentrations in the lungs and thus correct the neutrophil elastase:$\alpha_1$-PI imbalance in the lungs and prevent or slow destruction of lung tissue. Studies of normal and $\alpha_1$-PI deficient populations have suggested that the minimum protective serum $\alpha_1$-PI levels are 80 mg/dl or 11 $\mu$M (about 57 mg/dl; using pure standards). Consequently, most augmentation therapy in $\alpha_1$-PI deficient patients is aimed toward providing the minimum protective serum level of $\alpha_1$-PI, since serum $\alpha_1$-PI is the source of alveolar $\alpha_1$-PI.

Alpha$_1$-PI preparations have been available for therapeutic use since the mid 1980's. The major use has been augmentation (replacement) therapy for congenital $\alpha_1$-PI deficiency. The half-live of human $\alpha_1$-PI in vivo is 4.38 days with a standard deviation of 1.27 days. The currently recommended dosage of 60 mg $\alpha_1$-PI/kg body weight weekly will restore low serum levels of $\alpha_1$-PI to levels above the protective threshold level of 11 $\mu$M or 80 mg/dl.

Previously $\alpha_1$-PI has been purified by various techniques. One such process combined chromatography on an anion-exchange chromatography medium followed by PEG precipitation. Other purification procedures have used PEG precipitation followed by anion-exchange chromatography and others have used multiple PEG precipitation steps followed by anion-exchange chromatography. Still other methods have used phase separation techniques to purify $\alpha_1$-PI. Specific activities of 1.26 units/mg have been reported for purified $\alpha_1$-PI.

SUMMARY OF THE INVENTION

The present invention is directed to a process for purifying a,-proteinase inhibitor. The process comprises providing an impure protein fraction which comprises $\alpha_1$-proteinase inhibitor. The impure protein fraction is precipitated with a precipitant comprising PEG. In a preferred embodiment the precipitant further comprises $ZnCl_2$. The supernatant from the PEG precipitation, which comprises $\alpha_1$-proteinase inhibitor is collected and applied to an anion-exchange medium. A fraction comprising $\alpha_1$-proteinase inhibitor is recovered from the anion-exchange medium and applied to a metal chelate medium. A fraction comprising $\alpha_1$-proteinase inhibitor is then recovered from the metal chelate medium. In a preferred embodiment the fraction comprising $\alpha_1$-proteinase inhibitor recovered from the metal chelate medium is further purified by chromatography on a second ion-exchange medium.

Alpha$_1$-proteinase inhibitor purified by the process has a specific activity greater than 0.6 units/mg.

DETAILED DESCRIPTION

The present invention describes a purification process for the purification of $\alpha_1$-PI. This purification procedure uses a unique combination of known purification steps to produce a high specific activity $\alpha_1$-PI preparation.

Alpha$_1$-Proteinase Inhibitor Purification

Alpha$_1$-PI is purified from an impure protein fraction. The impure protein fraction may be plasma, $\alpha_1$-PI produced by recombinant methods or any other source comprising $\alpha_1$-PI protein. In a preferred embodiment $\alpha_1$-PI is prepared from frozen plasma. The plasma is thawed and the Cohn $IV_1+IV_4$ fraction is prepared. The preparation of the Cohn $IV_1+IV_4$ fraction (the Cohn $IV_1+IV_4$ precipitate) is well known in the art and is described briefly here.

Preparation of $IV_1+IV_4$ Fraction

Plasma is maintained at a temperature of 1.5° C. ±1.5° C. and the pH is adjusted to 7±0.2 with either sodium bicarbonate or acetate buffer, pH 4.0. Sufficient cold SD3A ethanol (95% v/v ethanol and 5% v/v methanol) is added to bring the plasma to a final alcohol concentration of 8% v/v. During the alcohol addition the temperature of the plasma is lowered to −2° C.±1° C. The precipitate which forms is removed by centrifugation in a Sharples or Westphalia centrifuge or by filtration through a filter press, at −2° C.±1° C. The result precipitate and supernatant are designated the Fraction I precipitate and supernatant.

The Fraction I supernatant is adjusted to pH 6.9±0.1 by the addition of pH 4 acetate buffer (0.8 M sodium acetate adjusted to pH 4 with acetic acid) and is brought to 20% v/v alcohol by the addition of cold SD3A alcohol. During the alcohol addition the temperature is lowered to −5.5° C.±1.5° C. The precipitate which forms is removed by centrifugation in a Sharples or Westphalia centrifuge or by filtration through a filter press, at −5.5° C.±1.5° C. The result precipitate and supernatant are designated the Fraction II+III precipitate and supernatant.

If required, the Fraction II+III supernatant is filtered through a 5 to 30 micron filter to remove particulate matter.

In one embodiment of the present invention, Antithrombin III (AT-III) Poor Fraction II and III is prepared as follows.

Heparin immobilized medium is equilibrated with 10 mM ±5 mM sodium citrate, pH 6.5–7.5 and then 10 mM±5 mM sodium citrate, pH 6.5–7.5, 150 mM±50 mM NaCl, 20% w/v SD3A alcohol. The medium is equilibrated in a −4° C. to −7° C. environment until the effluent is −4° C. to −7° C.

The Fraction II+III supernatant is passed through the heparin immobilized medium packed in a column. The medium adsorbed AT-III is washed with 10 mM ±5 mM sodium citrate, 150 mM ±50 mM NaCl, 2% w/v SD3A alcohol pH 6.5–7.5. The AT-III-poor effluent and the wash effluent are pooled and processed further.

Alternatively, the plasma suspension containing 8% v/v alcohol, at −2° C.±1° C., pH 7±0.2 described above is adjusted to pH 6.9±0.1 by the addition of pH 4 acetate buffer, and is then processed further without the removal of the precipitate. The alcohol concentration is raised to 20% v/v by the addition of cold SD3A alcohol and the temperature is gradually lowered to −5.5° C.±1.5° C. The precipitate which forms is removed by centrifugation in a Sharples or Westphalia centrifuge or by filtration through a filter press, at −5.5° C.±1.5° C. The resultant precipitate and supernatant are designated the Fraction I+II+III precipitate and supernatant.

The Fraction II+III, the Fraction II+III, AT-III poor and/or the Fraction I+II+III supernatant is/are maintained at −5.5° C.±1.5° C. and the pH is adjusted to 5.2±0.1 by the addition of pH 4 acetate buffer.

The resultant suspension is allowed to settle for at least 6 hours at −5.5° C.±1.5° C., after which time the pH is adjusted to 5.8±0.1 with either sodium acetate, pH 4.0 or sodium bicarbonate buffer, pH 4.0. The alcohol concentration is adjusted to 40% v/v by the addition of cold SD3A alcohol. The precipitate which forms is removed by centrifugation in a Sharples or Westphalia centrifuge or by filtration through a filter press, at −5.5° C.±1.5° C. The result precipitate and supernatant are designated the Fraction $IV_1$+$IV_4$ precipitate and supernatant. The Fraction $IV_1$+$IV_4$ precipitate is further purified for production of $\alpha_1$-PI.

The Fraction $IV_1$+$IV_4$ precipitate may be frozen until processed further or until sufficient material has been accumulated for further processing.

PEG/ZnCl$_2$ Precipitation

The $IV_1$+$IV_4$ precipitate is resuspended in water for injection (WFI), in a ratio of about 3 to 10 parts of water per part of $IV_1$+$IV_4$ precipitate, at about 0° to 10° C. and the pH is adjusted to 8.5±0.5 (the Water Extract). After the precipitate is resuspended solid Tris is added to a final concentration of 10±5 mM and NaCl (5±0.5 M) is added to a final concentration of 150±20 mM. Polyethylene glycol 3350 (PEG) and $ZnCl_2$ are added to a final concentration of 15±7.5% w/w PEG and 0.5±0.25 mM $ZnCl_2$. The suspension is adjusted to pH 8±1 and mixed for about one hour.

The PEG/$ZnCl_2$ precipitate which forms is removed by passing the suspension through a filter press at 0° C.–10° C. The filter press is washed before and after filtering with 150±25 mM NaCl, 15±7.5% w/w PEG and 5±5 mM $ZnCl_2$, pH 8±1. Alternatively, the precipitate may be removed by centrifugation at about 6,000 rpm for 10–15 minutes.

$ZnCl_2$ Precipitation $ZnCl_2$ (100±10 mM) is added to the supernatant (the 15% PEG-$ZnCl_2$ supernatant) to a final concentration of 10 ±5 mM and the solution is adjusted to pH 8±1. The solution is mixed for about one hour. The $ZnCl_2$ precipitate which forms is recovered by centrifugation, filter press, or other suitable method of recovery. The precipitate may be frozen for future processing.

For further processing the $ZnCl_2$ precipitate (the 10 mM $ZnCl_2$ precipitate) is re-solubilized in about 50 mM EDTA and adjusted to a conductivity of not more than 5 mS and to a pH of 8±1.

Anion-Exchange Chromatography

The re-solubilized $ZnCl_2$ precipitate is then applied to diethyl(2-hydroxypropyl)aminoethyl (QAE) chromatography medium or other similar anion-exchange medium. Either batch or column chromatography may be used. The medium is equilibrated at 0°–10° C. with cold water for injection (CWFI), prior to absorption of $\alpha_1$-PI to the chromatography medium. After $\alpha_1$-PI has been absorbed onto the medium it is washed with 50±25 mM NaCl, 10±5 mM sodium phosphate, pH 8±1 to remove unbound material. Alpha$_1$-PI is then eluted from the anion-exchange chromatography medium with 150±50 mM NaCl, 10±5 mM sodium phosphate, pH 8±1. The eluate which includes $\alpha_1$-PI (the 1st QAE Eluate) is collected for further processing.

After the removal of $\alpha_1$-PI, the anion-exchange medium is cleaned by washing with, in sequence: 2±0.2 M NaCl, 10±5 mM sodium phosphate, pH 8±1; WFI or 500 mM NaOH; WFI. The chromatography medium is then stored in either 2±0.2 M NaCl, 10±5 mM sodium phosphate, pH 8±1 or 50 mM NaOH until required.

SD Treatment

The anion-exchange medium eluate is concentrated/ diafiltered by ultrafiltration against 150±25 mM NaCl, 50±10 mM sodium phosphate, 1±0.1 mM imidazole, pH 7.5±1 to concentrate the $\alpha_1$-PI and to remove EDTA which co-elutes from the anion-exchange chromatography medium with the $\alpha_1$-PI, to form the 10K UF.

A solution of 10±1% w/v polysorbital 80 and 3±0.3% w/v tri-n-butyl phosphate is added to the diafiltered $\alpha_1$-PI to a final concentration of 1±0.5% w/v polysorbital 80 and 0.3±0.15% w/v tri-n-butyl phosphate. The solution is then incubated at 27°±3° C., pH 8±1 for 6.5±0.5 hours to inactivate any viruses which may be present in the $\alpha_1$-PI. After the incubation the treated $\alpha_1$-PI solution is cooled to 0°–10° C. and, if necessary, the pH is adjusted to 7.5±1. In other embodiments of the present invention the SD treatment is performed after ultrafiltration, as described below or the SD treatment may be performed at this step as well as at the step described below.

Metal Chelate Chromatography

The $\alpha_1$-PI is then applied to a copper, zinc or similar metal ion primed medium, such as MATREX-CELLUFINE CHELATE (supplied by Chisso of Japan), at 0°–10° C. Prior to use the medium is washed with, in sequence: WFI; 6±0.6 mg/ml $CuSO_4.5H_2O$; WFI and 150±25 mM NaCl, 250±25 mM sodium acetate, pH 5±1. The resin is then equilibrated with 150±25 mM NaCl, 50±10 mM sodium phosphate, 1±0.1 mM imidazole, pH 7.5±1 at 0°–10° C. Either batch or column chromatography can be used. The SD treated fraction is applied to the metal chelate chromatography medium to absorb $\alpha_1$-PI to the metal chelate chromatography medium. The $\alpha_1$-PI absorbed medium is washed with 500±50 mM NaCl, 50±10 mM sodium phosphate, 1±0.1 mM imidazole, pH 7.5±1 to remove any unbound material from the chromatography medium. The $\alpha_1$-PI is eluted with 150 ±25 mM NaCl, 50±10 mM sodium phosphate, 5±2.5 mM imidazole, pH 7.5±1. The $\alpha_1$-PI containing eluate (the $Cu^{++}$ Eluate) is collected and may be frozen until processed further.

The chromatography medium is cleaned with, and may be stored in, 500±50 mM NaCl, 50±25 mM EDTA, pH 7±1 or the medium may be washed with CWFI and cleaned with 500 mM NaOH and stored in 50 mM NaOH.

Ultrafiltration

The $\alpha_1$-PI containing eluate is ultrafiltered using a high (100,000) molecular weight cut-off ultrafiltration membrane, to remove high molecular weight contaminants and any viral contaminants which may be present in the metal chelate medium eluate.

The filtrate is collected and concentrated/diafiltered by ultrafiltration against 50±25 mM NaCl, 10±5 mM sodium phosphate, pH 8±1, containing up to 20 mM EDTA, to form the 100K UF.

SD Treatment

A solution of 10±1% w/v polysorbital 80 and 3±0.3% w/v tri-n-butyl phosphate is added to the diafiltered $\alpha_1$-PI to a final concentration of 1±0.5% w/v polysorbital 80 and 0.3±0.15% w/v tri-n-butyl phosphate. The solution is then incubated at 27°±3° C., pH 8±1 for 6.5±0.5 hours to inactivate any viruses which may be present in the $\alpha_1$-PI. After the incubation the treated $\alpha_1$-PI solution is cooled to 0°–10° C. and, if necessary, the pH is adjusted to 7.5±1.

Anion-Exchange Chromatography

The concentrated $\alpha_1$-PI is then applied to QAE chromatography medium or other similar anion-exchange medium, equilibrated at 0°–10° C. with CWFI, as described above. The chromatograph medium is then washed with 50±25 mM NaCl, 10±5 mM sodium phosphate, pH 8±1. Alpha$_1$-PI is eluted from the anion-exchange medium with 150±50 mM NaCl, 10±5 mM sodium phosphate, pH 8±1. The eluate (the 2nd QAE Eluate) is collected and its pH adjusted to 7.5±1. The eluate may be frozen until processed further. If necessary the eluate is concentrated by ultrafiltration.

The $\alpha_1$-PI is filtered through a 5 micron filter to remove any particulate matter. The concentration of the $\alpha_1$-PI is adjusted to a desired level and the $\alpha_1$-PI is sterile filtered through a 0.22 micron filter, dispensed into vials and lyophilized (the 5µ Filtrate).

The lyophilized $\alpha_1$-PI is redissolved in sterile water for injection for administration to patients (the Final Container).

Alpha$_1$-PI is stored at 2–8° C.

Alpha$_1$-PI Activity Assays

A chromogenic assay is used to detect $\alpha_1$-PI activity. The assay utilizes a trypsin sensitive chromogenic substrate which releases p-nitroaniline in the presence of trypsin (supplied by Sigma Chemical Co. of St Louis, Mo.). The p-nitroaniline released is detected at 405 nm. $\alpha_1$-PI inhibits the release of p-nitroaniline from the substrate. The activity of $\alpha_1$-PI in the product can be determined by reference to a standard $\alpha_1$-PI activity curve.

Protein Content

Protein content is determined by a Bio-Rad® assay method utilizing differential color change of a Coomassie Blue dye in response to various concentrations of protein measured at 595 nm. The protein content is calculated from a standard curve.

Administration

Alpha$_1$-PI is infused into a patient at a rate of about 0.08 ml/kg body weight per minute for the first 10 minutes. If the patient does not experience any discomfort, the rate is increased as tolerated. If tolerated, subsequent infusions to the same patient may be at the higher rate. If adverse events occur, the rate should be reduced or the infusion interrupted until the symptoms subside. The infusion may then be resumed at a rate which is tolerated by the patient.

If large doses are to be administered, several reconstituted vials of $\alpha_1$-PI may be pooled in an empty, sterile I.V. infusion container using aseptic technique.

Example 1

Purification of Alpha$_1$-PI

Twenty kg of $IV_1+IV_4$ precipitate was resuspended in 180 kg of WFI at 3.8° C. and the pH was adjusted to 8.94. After the precipitate was resuspended 242.3 g of Tris, 6.7 kg of 1 M NaCl, and 35.4 kg of PEG were added and the solution mixed for 60 minutes. Then 2.2 kg of 100 mM $ZnCl_2$ was added and the suspension was adjusted to pH 7.92 and mixed for an additional 60 minutes at 0–8° C.

The $PEG/ZnCl_2$ precipitate which formed was removed by passing the suspension through a filter press at 0–8° C. after the addition of 977 g of filtra-Cell BH 20 filter Aid (supplied by Celite of Germany). The filter press was washed before and after filtering with 30 kg of 150 mM NaCl, 15% w/w PEG, 0.5 mM $ZnCl_2$, pH 8.0.

27.8 kg of 100 mM $ZnCl_2$ was added to the supernatant and the solution was adjusted to pH 8. The precipitate which formed in the presence of the $ZnCl_2$ was recovered by centrifugation in a Sharples centrifuge. The $ZnCl_2$ precipitate was re-solubilized in 20 kg of 50 mM EDTA and adjusted to a conductivity of 6.48 mS and to a pH of 7.97.

The re-solubilized $ZnCl_2$ precipitate was then applied to diethyl(2-hydroxpropyl)aminoethyl (QAE) chromatography medium (supplied by Toso Haas) packed into a 20 l column with an internal diameter of 250 cm. The QAE medium was equilibrated at 4° C. with CWFI. The $\alpha_1$-PI was then absorbed into the chromatography medium. The chromatograph medium was then washed with 60 l of 50 mM NaCl, 10 mM sodium phosphate, pH 7.92. Alpha$_1$-PI was eluted from the anion-exchange medium with 60 l of 150 mM NaCl, 10 mM sodium phosphate, pH 8.06. The flow rate of the column was maintained at 600 ml/minute. The $\alpha_1$-PI containing eluate was collected.

The anion-exchange medium eluate was concentrated/diafiltered by ultrafiltration in a Millipore PELLICON unit (supplied by Millipore of Bedford Mass.) against 150 mM NaCl, 50 mM sodium phosphate, 1 mM imidazole, pH 7.5 to concentrate the $\alpha_1$-PI and to remove EDTA which co-elutes with the $\alpha_1$-PI.

1.1 kg of a solution of 10% w/v polysorbital 80 and 3% w/v tri-n-butyl phosphate was added to the diafiltered $\alpha_1$-PI and the solution was incubated at 25° C. for 1 hour to inactivate any viral contaminants present in the diafiltered $\alpha_1$-PI. The solution was then cooled to 4° C. and the pH adjusted to 7.33.

The $\alpha_1$-PI was then applied to 10 l of MATREX CEL-LUFINE CHELATE, a copper chelating medium (supplied by Chisso of Japan) at 4° C. Prior to use the medium was washed with, in sequence: WFI; 6 mg/ml $CuSO_4.5H_2O$; WFI and 150 mM NaCl, 250 mM sodium acetate, pH 5. The column was then equilibrated with 150 mM NaCl, 50 mM sodium phosphate, 1 mM imidazole, pH 7.5 at 4° C. The $\alpha_1$-PI absorbed medium was washed with 100 l of 500 mM NaCl, 50 mM sodium phosphate, 1 mM imidazole, pH 7.52 to remove any unbound material from the medium. The $\alpha_1$-PI bound to the chromatography medium was eluted with 150 mM NaCl, 50 mM sodium phosphate, 5 mM imidazole, pH 7.47. The flow rate was maintained at about 550 ml/minute. The $\alpha_1$-PI containing eluate was collected.

The eluate was ultrafiltered using a 100K CENTRA-SETTE supplied by Filtron. The filtrate was collected and concentrated/diafiltered by ultrafiltration in a Millipore PELLICON filtration unit against 50 mM NaCl, 20 mM EDTA, 10 mM sodium phosphate, pH 7.9.

The concentrated $\alpha_1$-PI was again applied to 5l of QAE chromatography medium, equilibrated at 0°–10° C. with CWFI, to absorb $\alpha_1$-PI to the chromatography medium. The chromatograph medium was then washed with 24l of 50 mM NaCl, 10 mM sodium phosphate, pH 8. Alpha$_1$-PI was eluted from the chromatography medium with 150 mM NaCl, 10 mM sodium phosphate, pH 8. The pH of the eluate was adjusted to 7.5. The eluate was concentrated/diafiltered by ultrafiltration in a Millipore PELLICON filtration unit against 50 mM NaCl, 10 mM sodium phosphate, pH 7.9.

Throughout the purification, aliquots of the $\alpha_1$-PI containing solutions were collected and analyzed. The results are summarized in Table I.

TABLE I

| Sample | $\alpha_1$-PI Activity (%) | $A_{280\,nm}$ (kg) | U $A_{280\,nm}$ (%) | Specific Activity (U/mg) |
|---|---|---|---|---|
| Water | 3,460 | 31.3 | 156,500 | 0.022 |
| Extract | (100) | (5,000) | (100) | |
| 15% PEG-ZnCl$_2$ | 2,478 | 5.22 | 26,507 | 0.093 |
| Supernatant | (72) | (5,078) | (17) | |
| 10 mM ZnCl$_2$ | 2,322 | 7.72 | 27,792 | 0.084 |
| Precipitate | (67) | (3,600) | (18) | |
| 1st QAE | 1,612 | 3.95 | 11,882 | 0.136 |
| Eluate | (47) | (3,008) | (8) | |
| 10 K UF | 1,764 | 19.5 | 11,720 | 0.151 |
| | (51) | (601) | (7) | |
| Cu$^{++}$ Eluate | 1,445 | 1.08 | 3,521 | 0.443 |
| | (42) | (3,261) | (2) | |
| 100 K UF | 1,371 | 0.59 | 3,184 | 0.431 |
| | (40) | (5,396) | (2) | |

TABLE I-continued

| Sample | $\alpha_1$-PI Activity (%) | $A_{280\,nm}$ (kg) | U $A_{280\,nm}$ (%) | Specific Activity (U/mg) |
|---|---|---|---|---|
| 10 K UF | 1,406 | 5.98 | 3,007 | 0.467 |
| | (41) | (503) | (2) | |
| 2nd QAE | 1,181 | 2.13 | 1,787 | 0.661 |
| Eluate | (34) | (839) | (1) | |

The purification procedure produced a final $\alpha_1$-PI fraction with a specific activity of 0.661 U/mg and a yield of 34%.

Example 2

The purification procedure described in Example 1 was repeated except the $\alpha_1$-PI was filtered through a 0.22 micron filter. The filtrate was then dispensed into sterile vials and lyophilized.

The results are summarized in Table II.

TABLE II

| Sample | $\alpha_1$-PI Activity (%) | $A_{280\,nm}$ (kg) | U $A_{280\,nm}$ (%) | Specific Activity (U/mg) |
|---|---|---|---|---|
| Water | 75,800 | 16.8 | 3,360,000 | 0.023 |
| Extract | (100) | (200) | (100) | |
| 15% PEG-ZnCl$_2$ | 45,713 | 1.58 | 394,684 | 0.116 |
| Supernatant | (60) | (249.8) | (12) | |
| 10 mM ZnCl$_2$ | 30,995 | 9.03 | 301,602 | 0.103 |
| Precipitate | (41) | (33.4) | (9) | |
| 1st QAE | 36,762 | 1.87 | 112,574 | 0.327 |
| Eluate | (49) | (60.2) | (3) | |
| 10 K UF | 26,938 | 11.34 | 109,998 | 0.336 |
| | (49) | (9.7) | (3) | |
| After S/D | 34,906 | 11.81 | 127,548 | 0.274 |
| Treatment | (46) | (10.8) | (4) | |
| Cu$^{++}$ Eluate | 23,435 | 0.76 | 45,904 | 0.510 |
| | (31) | (60.4) | (1) | |
| 100 K UF | 21,952 | 0.45 | 40,320 | 0.545 |
| | (29) | (89.6) | (1) | |
| 10 K UF | 21,859 | 3.43 | 37,696 | 0.580 |
| | (29) | (10.99) | (1) | |
| 2nd QAE | 10,270 | 1.14 | 21,204 | 0.909 |
| Eluate | (25) | (18.6) | (1) | |
| 10 K UF | 24,461 | 10.99 | 26,926 | 0.909 |
| | (32) | (2.45) | (1) | |
| 5$\mu$ | 21,648 | 10.94 | 27,109 | 0.799 |
| Filtration | (29) | (2.478) | (1) | |
| Final | 17,850 | 11.02 | 23,142 | 0.773 |
| Container | (24) | (2.1) | (1) | |

The purification procedure produced a final $\alpha_1$-PI fraction with a specific activity of 0.773 U/mg and a yield of 24%.

Example 3

Stability of the Purified Alpha$_1$-PI

Final container samples of $\alpha_1$-PI were stored in temperature controlled incubators at 5° C. After three months, storage samples were analyzed and compared to samples analyzed prior to storage. After reconstitution, the samples were incubated at 20° C. for 0, 2 or 4 hours prior to analysis. Results for storage at 5° C. for 0 and 3 months are summarized in Table III.

TABLE III

| Test Description | Months of storage at 5° C. | |
|---|---|---|
| | 0 | 3 |
| $\alpha_1$-PI activity | 205 U/vial | 203 U/vial |
| $\alpha_1$-PI Activity after reconstitution: | | |
| 0 hours | 213 U/vial | 203 U/vial |
| 2 hours | 223 U/vial | 210 U/vial |
| 4 hours | 188 U/vial | 208 U/vial |
| Elastase inhibitory activity after reconstitution | | |
| 0 hours | 323 U/vial | 323 U/vial |
| 2 hours | 305 U/vial | 298 U/vial |
| 4 hours | 318 U/vial | 308 U/vial |
| Protein content | 0.440 g/vial | 0.453 g/vial |
| Physical | | |
| Appearance | Pass | Pass |
| Moisture | 0.50% w/w | 0.37% w/w |
| Solubility | 1 minute | 1 minute |
| Vacuum | Present | Present |

After 3 months of storage at 5° C., samples of $\alpha_1$-PI retained 99% of their original activity. At manufacture, $\alpha_1$-PI activity of samples at 0, 2 or 4 hours after reconstitution was 213, 223, and 188 U/vial, respectively. Following storage at 5° C. for 3 months the $\alpha_1$-PI activity following reconstitution was 203, 210, and 208 U/vial at 0, 2 and 4 hours, respectively.

Elastase inhibitory activity was also measured following reconstitution of the samples. At the time of manufacture, elastase inhibitory activity at 0, 2 or 4 hours after reconstitution was 323, 305, and 318 U/vial, respectively. Following storage for 3 months at 5° C., the elastase inhibitory activity was 323, 298, and 308 U/vial at 0, 2 or 4 hours after reconstitution, respectively.

Moisture content of the $\alpha_1$-PI sample at manufacture was 0.50% and after 3 months of storage at 5° C. it was 0.37%.

Further experiments have shown that alpha$_1$-PI remains stable for at least 9 months following storage at 5° C. Samples stored at 5° C. retained 99% of their original $\alpha_1$-PI activity.

Example 4

Comparison of $\alpha_1$-PI and Commercially Available $\alpha_1$-PI $\alpha_1$-PI prepared in Example 2 was analyzed and compared to commercially available $\alpha_1$-PI obtained from the Cutter Biological division of Miles, Inc. The protein composition of the samples were analyzed by radial immunodiffusion.

TABLE IV

| Protein | $\alpha_1$-PI prepared in Example 2 mg/ml (% Total) | Cutter 01J081 mg/ml (% Total) | Cutter 01K047 mg/ml (% Total) |
|---|---|---|---|
| Major Proteins | | | |
| $\alpha_1$-PI | 23.80(95) | 29.19(91) | 35.14(91) |
| Haptoglobin | 1.13 (5) | 0.60 (2) | 0.68 (2) |
| Albumin | <0.50 | 1.53 (5) | 2.27 (6) |
| IgA | <0.01 | 0.92 (3) | 0.90 (2) |

TABLE IV-continued

| Protein | $\alpha_1$-PI prepared in Example 2 mg/ml (% Total) | Cutter 01J081 mg/ml (% Total) | Cutter 01K047 mg/ml (% Total) |
|---|---|---|---|
| Minor Proteins | | | |
| $\alpha_1$-Antichymotrypsin | <0.171 | <0.171 | <0.171 |
| $\alpha_2$-Antiplasmin | 0.041 | 0.083 | 0.106 |
| $\alpha_2$-Macroglobulin | <0.50 | <0.50 | <0.50 |
| Antithrombin III | <0.060 | 0.192 | 0.35 |
| Apolipoprotein A1 | 0.06 | 0.21 | 0.17 |
| Apoliprotein B | <0.095 | <0.095 | <0.095 |
| C1-Inactivator | <0.045 | 0.091 | 0.101 |
| Ceruloplasmin | <0.100 | <0.100 | <0.100 |
| HMW Kininogen | 0.009 | <0.001 | <0.001 |
| IgG | <0.020 | <0.020 | <0.020 |
| Prealbumin | 0.05 | <0.05 | <0.05 |
| Protein-C | <0.00125 | <0.00125 | <0.00125 |
| Protein-S | <0.001 | <0.001 | <0.001 |
| Transferrin | <0.50 | <0.50 | <0.50 |

% Total = Percent of the Major Immunologically-Detected Plasma Proteins

Example 5

In Vivo Use of Alpha$_1$-PI

A group of three rabbits was administered $\alpha_1$-PI intravenously over a period of approximately one minute at a dose of 240 mg/kg of body weight (4 times the clinical dose of 60 mg/kg of body weight). A control rabbit was injected with 2.73 ml/kg body weight of 750 mM NaCl, 50 mM sodium phosphate, pH 7.5, over a period of one minute. Clinical observations were recorded immediately after administration and again at 30 and 72 hours after administration. Body weights were recorded prior to infusion and at the end of the infusion. A gross necropsy was performed on all animals at the completion of the study.

Clinical signs observed in the $\alpha_1$-PI-treated group included decreased activity and dyspnea. There was no apparent effect on mean body weight of the animals in any group during this study. None of the rabbits died in the $\alpha_1$-PI-treated groups when a dose equivalent to 240 mg $\alpha_1$-PI/kg of body weight (4 times the clinical dose of 60 mg/kg of body weight) was given. Furthermore, no visible lesions were observed in any of the animals at terminal necropsy.

Alpha$_1$-PI was non-toxic when administered intravenously at a dose of 240 mg/kg of body weight (4 times the clinical dose of 60 mg/kg of body weight).

Example 6

In Vivo Use of Alpha$_1$-PI

A group of three mice were administered $\alpha_1$-PI intravenously over a period of approximately one minute at a dose of 1500 mg/kg of body weight (25 times the clinical dose of 60 mg/kg of body weight). A group of three control mice were injected with 17.0 ml/kg of body weight, 750 mM NaCl, 50 mM sodium phosphate pH 7.5, over a period of one minute. Clinical observations were recorded immediately after dosing and again at 24, 48 and 72 hours. Body weights were recorded prior to the infusion and at the end of the infusion. A gross necropsy was performed on all animals at the completion of the study.

The only clinical sign observed was decreased activity. There was no apparent effect on mean body weight of the animals during this study. None of the mice died when a dose of equivalent to 1,500 mg $\alpha_1$-PI/kg of body weight (25 times the clinical dose of 60 mg/kg of body weight) was given. Furthermore, no visible lesions were observed in any of the animals at terminal necropsy.

Based upon the results from the acute intravenous toxicity study in mice, $\alpha_1$-PI was found to be non-toxic when administered intravenously at 1,500 mg/kg of body weight (25 times the clinical dose of 60 mg/kg of body weight).

Example 7

In Vivo Use of Alpha$_1$-PI

A rabbit study lasting 33 days was designed to evaluate the potential toxic effect(s) associated with repeated intravenous exposure to $\alpha_1$-PI. For this study, five consecutive daily injections at twice the anticipated clinical dose of 60 mg/kg of body weight were administered. Preliminary hematological, clinical, biochemical, and gross necropsy data obtained from animals at day 6 and day 33 after the fifth repeated intravenous infusion of $\alpha_1$-PI were obtained. Alpha$_1$-PI was prepared by reconstitution of lyophilized powder with 5 ml Sterile Water for Injection to a concentration of 88 mg $\alpha_1$-PI/ml. A 5X buffer (750 mM NaCl, 50 mM sodium phosphate, pH 7.5) containing a concentration of salt similar to that within the reconstituted test-article served as the control. Male and female Albino New Zealand White rabbits (2.0 to 3.0 kg) were used as the test and control recipients.

Twelve (12) rabbits were administered intravenous equivalent-volume injections of either a 5X buffer (6 animals) or $\alpha_1$-PI (6 animals) at a dose of 120 mg (1.4 ml)/kg. Infusions of the 5X buffer and $\alpha_1$-PI were repeated daily for five consecutive days. The animals were separated into two sex-matched groups of six animals, three received control solution and three received the $\alpha_1$-PI solution. Each group of six animals were evaluated at day 6 and day 33 after commencement of the infusions. Following each infusion, all rabbits were observed at 30 and 60 minutes, then hourly for four hours. After the last infusion, the animals were monitored daily for pharmacotoxic signs and mortality.

Repeated administration of $\alpha_1$-PI at 120 mg/kg of body weight (two-times the clinical dose of 60 mg/kg of body weight) or an equal volume of 5X buffer control for five consecutive days, resulted in no significant perturbations in hematologic, clinical or biochemical parameters among rabbits examined at day 6 or day 33 after administration of the final dose.

The present invention is not limited to the specific embodiment given. It will be obvious to one skilled in the art that variations, such as variations in buffer concentration and types of buffers and salts, could also be used. Therefore, the present invention is not intended to be limited to the working embodiments described above. The scope of the invention is defined in the following claims.

What is claimed is:

1. A process for purifying $\alpha_1$-proteinase inhibitor comprising:

providing an impure protein fraction comprising $\alpha_1$-proteinase inhibitor;

suspending the impure protein fraction comprising $\alpha_1$-proteinase inhibitor in water;

precipitating the impure protein fraction comprising $\alpha_1$-proteinase inhibitor with a precipitant comprising polyethylene glycol (PEG) and $ZnCl_2$;

collecting the supernatant from the PEG/$ZnCl_2$ precipitation, wherein the supernatant comprises $\alpha_1$-proteinase inhibitor;

precipitating $\alpha_1$-proteinase inhibitor from the PEG/$ZnCl_2$ supernatant with $ZnCl_2$ at a concentration of 5 to 15 mM to thereby provide an $\alpha_1$-proteinase inhibitor precipitate;

resuspending the $\alpha_1$-proteinase inhibitor precipitate in an aqueous medium;

applying the resuspended $\alpha_1$-proteinase inhibitor to an anion-exchange chromatography medium;

applying $\alpha_1$-proteinase inhibitor recovered from the anion-exchange chromatography medium to a metal chelate medium; and recovering a fraction comprising $\alpha_1$-proteinase inhibitor from the metal chelate medium.

* * * * *